United States Patent [19]

Ulyanov

[11] 3,973,190
[45] Aug. 3, 1976

[54] INFRALOW FREQUENCY TRANSFER FUNCTION ANALYZER

[76] Inventor: Lev Petrovich Ulyanov, Eropkinsky pereulok, 7, kv. 6, Moscow, U.S.S.R.

[22] Filed: Aug. 13, 1973

[21] Appl. No.: 387,809

[52] U.S. Cl. .......................... 324/78 R; 324/158 R
[51] Int. Cl.² ..................................... G01R 23/00
[58] Field of Search ............ 324/158 R, 78 R, 77 R, 324/77 A

[56] References Cited
UNITED STATES PATENTS
3,611,129  10/1971  Simurda ........................... 324/78 R

*Primary Examiner*—R. V. Rolinec
*Assistant Examiner*—Ernest F. Karlsen
*Attorney, Agent, or Firm*—Haseltine, Lake & Waters

[57] ABSTRACT

An infralow frequency controlled-member transfer function analyzer comprises an electromechanical infralow frequency generator, a rotary transformer mechanically coupled to the output shaft of the electromechanical infralow frequency generator, a matching amplifier, two modulators similar to each other, a differentiator connected to the output of the matching amplifier and through one modulator to one rotor winding of the rotary transformer, a matching filter connected to the output of the matching amplifier in parallel with the differentiator and through the second modulator to the other rotor winding, an A.C. voltage amplifier connected to one stator winding of the rotary transformer and to a servomotor which drives the rotary transformer stator carrying a means indicating the phase angle of the signal at the output of the plant under investigation, an indicating instrument connected through a switch to the other stator winding of the rotary transformer, and a second rotary transformer the stator of which is mechanically coupled to the stator of the first rotary transformer while its stator windings are alternately connected through a switch to the indicating instrument. One rotor winding is connected to a matching resistor and the other rotor winding, to the second stator winding of the first rotary transformer.

2 Claims, 7 Drawing Figures

INFRALOW FREQUENCY TRANSFER FUNCTION ANALYZER

FIELD OF INVENTION

The invention relates to test and measuring instruments and to process control systems, more particularly, to infralow frequency controlled-member transfer function analyzers.

BACKGROUND

The invention can be used for investigating viscoelastic properties of various substances, such as polymers within a wide range of infralow frequencies. Besides the analyzer can be used as a differential vector resolver of harmonic oscillations in various analogue computers.

There exist various infralow frequency transfer function analyzers. One existing infralow frequency transfer function analyzer uses an infralow frequency generator, multipliers and integrators.

A disadvantage of this type of infralow frequency transfer function analyzer is that it depends for its operation on integrating the product of disturbance amplitude by the response of the member under investigation to the disturbance during the period of the disturbance signal, which makes the analysis at low frequencies a very lengthy process.

For example, at frequencies of the order of $10^{-6}$ Hz the minimum measurement time would be 11 days. Obviously, apart from a considerable waste of time, it is hardly feasible to insure the required reliability and accuracy of measurements.

In the first place, this is due to the difficulties in meeting the requirements to the drift of the integrators, because of which reliable measurements cannot be made at frequencies below $10^{-5}$ Hz.

Besides, two multipliers and two integrators have to be used for the analysis of one signal and the measurement results require mathematical processing for determining an amplitude-frequency and a phase-frequency characteristic of the controlled member.

There also exists a transfer function analyzer comprising an electromechanical infralow frequency generator, a rotary transformer mechanically coupled to the output shaft of the electromechanical infralow frequency generator, a modulator connected to the rotary transformer and an indicating instrument.

A disadvantage of such type of transfer function analyzers is that they too require much time for measuring the characteristics of the signal being analyzed at infralow frequencies.

SUMMARY OF INVENTION

An object of the invention is to obviate the above disadvantages by providing an infralow frequency controlled-member transfer function analyzer which enables the characteristics of the analyzed signal, such as phase, amplitude, real and imaginary components to be measured within shorter time periods.

With this object in view, there is provided an infralow frequency controlled-member transfer function analyzer comprising an electromechanical infralow frequency generator, a rotary transformer mechanically coupled to the output shaft of the electromechanical infralow frequency generator, a modulator connected to the rotary transformer and an indicating instrument reading the amplitude of the signal at the output of the member under investigation. According to the invention, the apparatus includes a matching amplifier, a differentiator connected to the matching amplifier and through the modulator to the rotor winding of the rotary transformer, a smoothing filter connected to the matching amplifier in parallel with the differentiator and through a second modulator to the second rotor winding of the rotary transformer, while one stator winding of the rotary transformer is connected to an A.C. voltage amplifier which is also connected to a servomotor driving the stator of the rotary transformer carrying a means for indicating the phase angle of the analyzed signal at the output of the member under investigation, the other stator winding of the rotary transformer being connected through a switch to the indicating instrument.

The infralow frequency analyzer preferably comprises a second rotary transformer, the stator of which is mechanically coupled to the stator of the first rotary transformer, while the stator windings of the second rotary transformer are alternately connected through a switch to the indicating instrument and one rotor winding of the second rotary transformer is shorted through a matching resistor, the other rotor winding being connected to the second stator winding of the first rotary transformer.

The use of the infralow frequency controlled-member transfer function analyzer reduces the time required for measuring the characteristics of the analyzed signal at the controlled-plant output, improves the accuracy of signal measurements, extends the frequency range within which the characteristics of the analyzed signal can be measured towards lower frequencies and increases the number of signal characteristics that can be measured.

BRIEF DESCRIPTION OF DRAWING

The invention will be better understood from the following description of its specific embodiment when read in connection with the accompanying drawings, in which.

DETAILED DESCRIPTION

A controlled member 1 (FIG. 1), which may be any four-terminal network whose amplitude-frequency and phase-frequency characteristics are being analyzed within a wide range of infralow frequencies and which is not included within the infralow frequency transfer function analyzer, but is only disclosed in the specification to elucidate the operation of the invention, is connected via a matching amplifier 2, provided with an output filter, to a differentiator 3 and a smoothing filter 4 connected in parallel. The controlled member may be, for example, an electric, mechanical or electromechanical device or the like for investigating the viscoelastic properties of polymers or as a vector resolver of harmonic oscillations in analogue computers. Member 1 may produce signals indicating disturbances, for example, at a frequency of $10^{-6}$Hz. A minimum measurement time may be, for example, eleven days.

Figure 1:
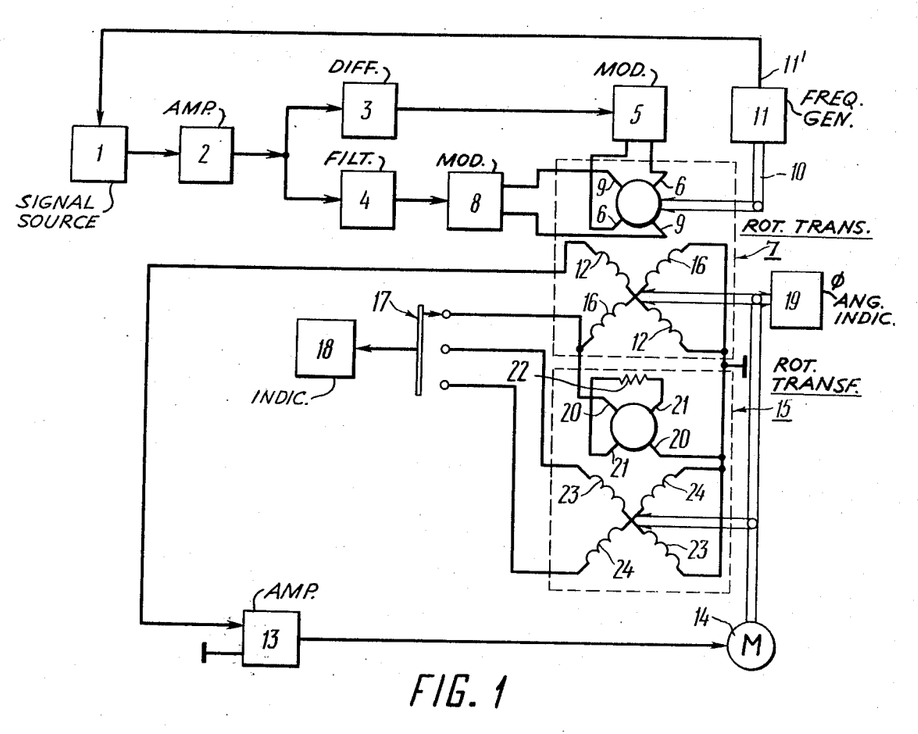
FIG. 1 is a functional-circuit diagram of an infralow frequency transfer function analyzer, according to the invention.

The differentiator 3 shifts the phase of the voltage applied from the output of the matching amplifier 2 by 90° relative to the phase of the output voltage of the smoothing filter 4. The differentiator 3 is connected through a modulator 5 to a rotor winding 6 of a rotary transformer 7. The smoothing filter 4 is connected through a modulator 8 to a rotor winding 9 of the rotary transformer 7. The modulators 5 and 8 are similar to each other.

The rotor of the rotary transformer 7 is mechanically coupled with an output shaft 10 of an electromechanical infralow frequency generator 11, an output 11' of the generator being connected to the member 1 under investigation.

A stator winding 12 of the rotary transformer 7 is connected to an amplifier 13 feeding into a servomotor 14 which drives the stator of the rotary transformer 7 and the stator of a rotary transformer 15.

A stator winding 16 of the rotary transformer 7 is connected through a switch 17 to an indicating instrument 18. The stator of the rotary transformer 7 is mechanically coupled with a means 19 which indicates the phase angle of the signal at the output of the plant 1 under investigation. The plant 1 produces a signal. This signal may be generated originally within the plant 1 or may be a modification of a signal which is produced in the infralow frequency generator 11 and transmitted to the plant 1 whereat the signal is modified. In any event the plant 1 produces a signal which varies for example in phase and/or amplitude according to the process going on in the plant 1.

Figure 2:
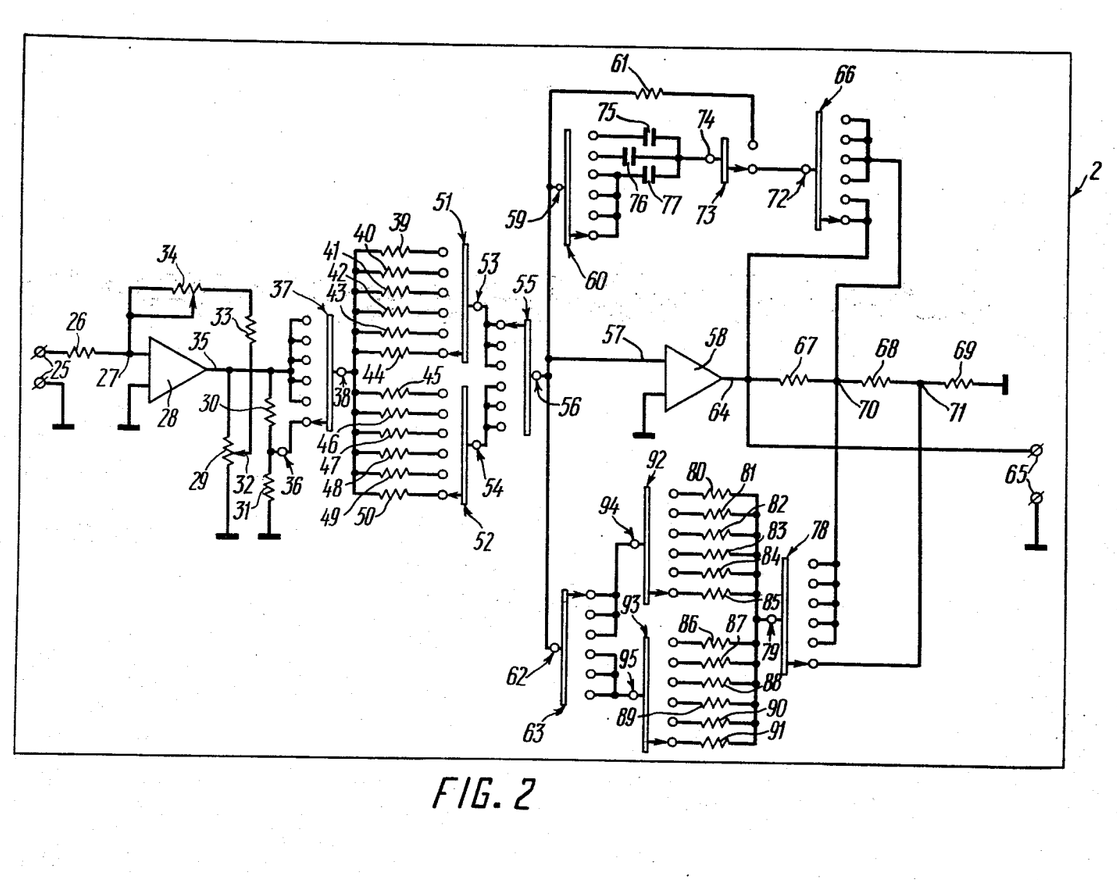
FIG. 2 is a circuit diagram of a matching amplifier, according to the invention.

A rotor winding 20 of the rotary transformer 15 is connected to the stator winding 16 of the rotary transformer 7. A rotor winding 21 of the rotary transformer 15 is connected to a matching resistor 22. A stator winding 23 and a stator winding 24 of the rotary transformer 15 are alternately connected to the indicating instrument 18 through the switch 18:

Said matching amplifier 2 is designed as follows.

An input 25 (FIG.2) of the matching amplifier 2 is connected through a resistor 26 to an input 27 of an operational amplifier 28 feeding into a precision potentiometer 29 and into series-connected resistors 30, 31.

A slider 32 of the precision potentiometer 29 is connected through a series combination of a resistor 33 and a matching variable resistor 34 to the output 27 of the operational amplifier 28 so as to form a feedback circuit.

Outputs 35 and 36 of the operational amplifier 28 are connected to a decade switch 37. The term "decade switch" used above and hereinafter means a switch which varies the value of a parameter by a factor of 10.

A common terminal 38 of the decade switch 37 is connected to resistors 39, 40, 41, 42, 43, 44 and to resistors 45, 46, 47, 48, 49, 50. The resistors 39, 40, 41, 42, 43, 44 are connected to an intradecade switch 51. The term "intradecade switch" used above and hereinafter means a switch which varies the value of a parameter inside one decade. Resistors 45, 46, 47, 48, 49 and 50 are connected to an intradecade switch 52.

A common terminal 53 of the intradecade switch 51 and a common terminal 54 of the intradecade switch 52 are connected to a decade switch 55, a common terminal 56 thereof being connected to an input 57 of an operational amplifier 58, to a common terminal 59 of a decade switch 60, to a resistor 61 and to a common terminal 62 of a decade switch 63.

An output 64 of the operational amplifier 58 is connected to an output 65 of the matching amplifier 2 (FIG.1), to a decade switch 66 (FIG.2) and to a resistor 67. Series-connected resistors 67, 68 and 69 form a decade voltage divider at the output of the operational amplifier 58 with voltage outputs 70, 71. The output 70 is connected to the decade switch 66, a common terminal 72 thereof being connected to a switch 73 which is also connected to the resistor 61. A common terminal 74 of the switch 73 is connected to capacitors 75, 76 and 77, connected in turn to the decade switch 60.

The outputs 70 and 71 are connected to a decade switch 78. A common terminal 79 of the decade switch 78 is connected to resistors 80, 81, 82, 83, 84 and 85 and to resistors 86, 87, 88, 89, 90 and 91. The resistors 80, 81, 82, 83, 84 and 85 are connected to an intradecade switch 52; the resistors 86, 87, 88, 89, 90 and 91 are connected to an intradecade switch 93. A common terminal 94 of the intradecade switch 92 and a common terminal 95 of the intradecade switch 93 are connected to the decade switch 63.

The output 65 of the matching amplifier 2 (FIG.1) is connected to an input 96 (FIG.3) of the differentiator 3.

Figure 3:
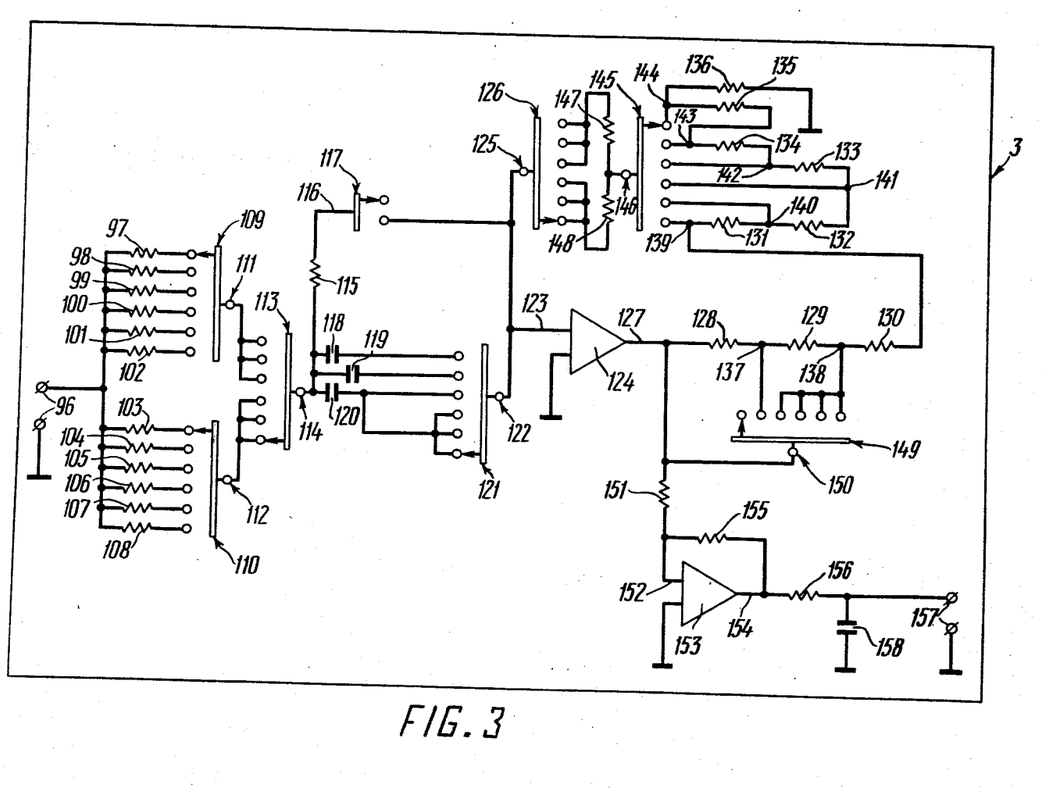
FIG. 3 is a circuit diagram of a differentiator, according to the invention.

The input 96 of the differentiator 3 is connected to resistors 97, 98, 99, 100, 101 and 102 and to resistors 103, 104, 105, 106, 107 and 108. The resistors 97, 98, 99, 100, 101 and 102 are connected to an intradecade switch 109; the resistors 103, 104, 105, 106, 107 and 108 are connected to an intradecade switch 110. A common terminal 111 of the intradecade switch 109 and a common terminal 112 of the intradecade switch 110 are connected to a decade switch 113. A common terminal 114 of the decade switch 113 is connected through a resistor 115 to a common terminal 116 of a switch 117 and to capacitors 118, 119 and 120. The capacitors 118, 119 and 120 are connected to a decade switch 121. A common terminal 122 of the decade switch 121 is connected to an input 123 of an operational amplifier 124, to the switch 117 and to a common terminal 125 of a decade switch 126.

Connected to an output 127 of the operational amplifier 124 is a series combination of resistors 128, 129, 130, 131, 132, 133, 134, 135 and 136 which form a voltage divider at the output of the operational amplifier 124 and have outputs 137, 138, 139, 140, 141, 142, 143 and 144. The outputs 139, 140, 141, 142, 143 and 144 are connected to an intradecade switch 145. A common terminal 146 of the intradecade switch 145 is connected to the decade switch 126 through resistors 147 and 148.

The outputs 137 and 138 are connected to a decade switch 149 a common terminals 145 thereof being connected to the output 127 of the operational amplifier 124.

The output 127 of the operational amplifier 124 is connected to an input 152 of an operational amplifier 153 through a resistor 151. An output 154 of the operational amplifier 153 is connected to the input 152 through a feedback resistor 155. The output 154 of the operational amplifier 153 is connected through a resistor 156 to an output 157 of the differentiator 3 by-passed by capacitors 158.

Connected to the output of the matching amplifier 2 (FIG. 1) in parallel with the differentiator 3 is the smoothing filter 4.

An input 159 (FIG. 4) of the smoothing filter 4 is connected to resistors 160, 161, 162, 163, 164 and 165 and to resistors 166, 167, 168, 169, 170 and 171. The resistors 160, 161, 162, 163, 164 and 165 are connected to an intradecade switch 172; the resistors 166, 167, 168, 169, 170 and 171 are connected to an infradecade switch 173. A common terminal 174 of the intradecade switch 172 and a common terminal 175 of the intradecade switch 173 are connected to a decade switch 176. A common terminal 177 of the decade switch 176 is connected to an input 178 of an operational amplifier 179, to a switch 180, to resistors 181, 182, 183, 184, 185 and 186, connected to an infradecade switch 187 and to resistors 188, 189, 190, 191, 192 and 193 connected to an intradecade switch 194. A common terminal 195 of the intradecade switch 187 and a common terminal 196 of the intradecade switch 194 are connected to a decade switch 197.

Figure 4:
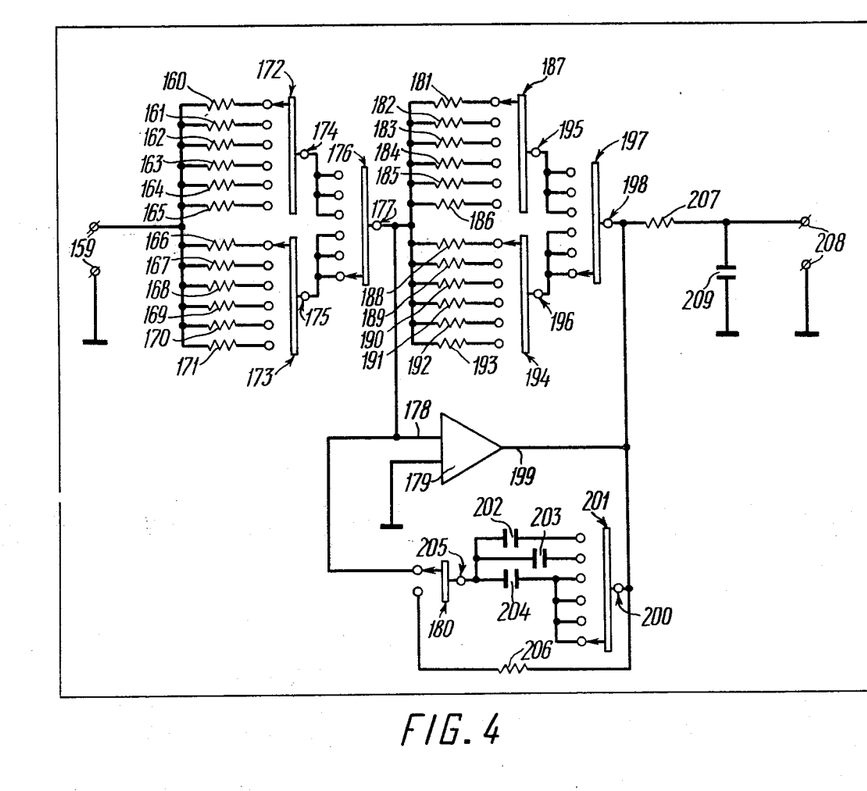
FIG. 4 is a circuit diagram of a smoothing filter, according to the invention.

A common terminal 198 of the decade switch 197 is connected to an output 199 of the operational amplifier 179 and to a common terminal 200 of a decade switch 201.

The decade switch 201 is connected to capacitors 202, 203, 204 connected to a common terminal 205 of the switch 180.

The output 199 of the operational amplifier 179 is connected through a resistor 206 to the switch 180 and through a resistor 207 to an output 208 of the smoothing filter 4 (FIG. 1) by-passed by a capacitor 209 (FIG. 4).

The decade switches 37, 55, 60, 63, 66 and 78 (FIG. 2) of the matching amplifier 2 (FIG. 1), the decade switches 113, 121, 126 and 149 (FIG. 3) of the differentiator 3 (FIG. 1), the decade switches 176, 179 and 201 (FIG. 4) of the smoothing filter 4 (FIG. 1) are mounted on one shaft (not shown).

The intradecade switches 51, 52, 92 and 93 (FIG. 2) of the matching amplifier 2 (FIG. 1), the intradecade switches 109, 110, 145 (FIG. 3) of the differentiator 3 (FIG. 1) and the intradecade switches 172, 173, 187 and 200 (FIG. 4) of the smoothing filter 4 (FIG. 1) are mounted on one shaft (not shown).

The switch 73 (FIG. 2) of the matching amplifier 2 (FIG. 1), the switch 117 (FIG. 3) of the differentiator 3 (FIG. 1) and the switch 180 (FIG. 4) of the smoothing filter 4 (FIG. 1) are mounted on one shaft (not shown).

The output 157 (FIG. 3) of the differentiator 3 is connected to an input 210 (FIG. 5) of the modulator 5 (FIG. 1) similar to the modulator 8.

The input 210 (FIG. 5) of the modulator 2 is connected to a winding 211 of a transformer 212 through a diode bridge including diodes 213, 214, 215 and 216, resistors 217, 218 and a potentiometer 219 and to a winding 220 of the transformer 212 through a diode bridge including diodes 221, 222, 223 and 224, resistors 225 and 226 and a potentiometer 227.

Figure 5:
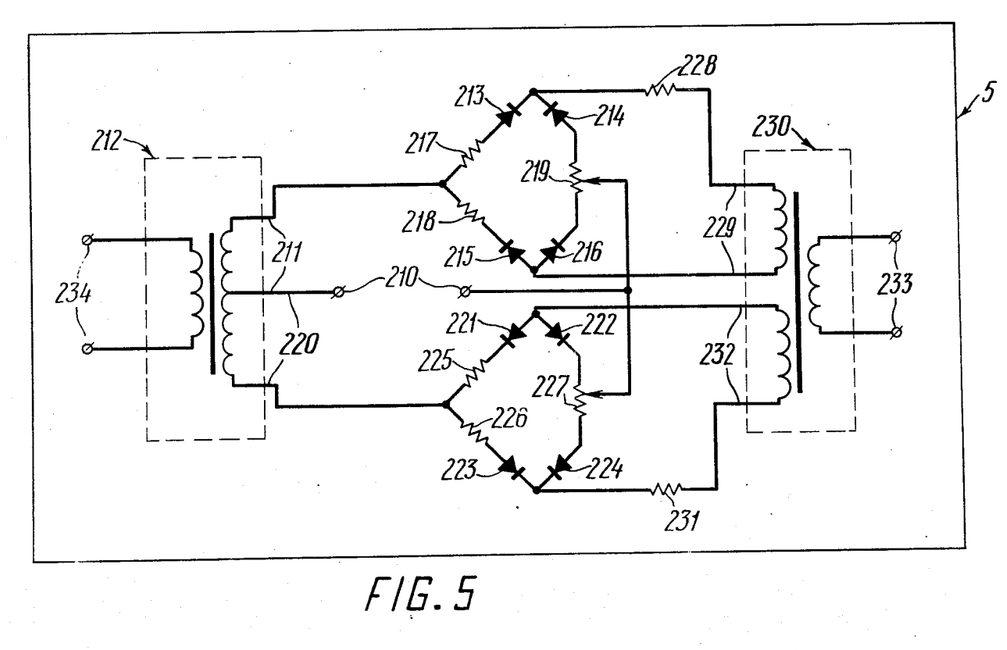
FIG. 5 is a circuit diagram of a modulator, according to the invention.

The diode bridge which includes the diodes 213, 214, 215 and 216, the resistors 217 and 218 and the potentiometer 219 is connected through a ballast resistor 228 to a winding 229 of a transformer 230.

The diode bridge which includes the diodes 221, 222, 223 and 224, the resistors 225 and 226, and the potentiometer 270 is connected through a ballast resistor 231 to a winding 232 of the transformer 230.

An input 233 of the transformer 230 is connected to a reference voltage source (not shown). An output 234 of the transformer 212 is the output of the modulator 5 (FIG. 1) which is connected to the rotor winding 6 of the rotary transformer 7. The stator winding 12 of the rotary transformer 7 is connected to an input 235 (FIG. 6) of the A.C. voltage amplifier 13 (FIG. 1).

Figure 6:
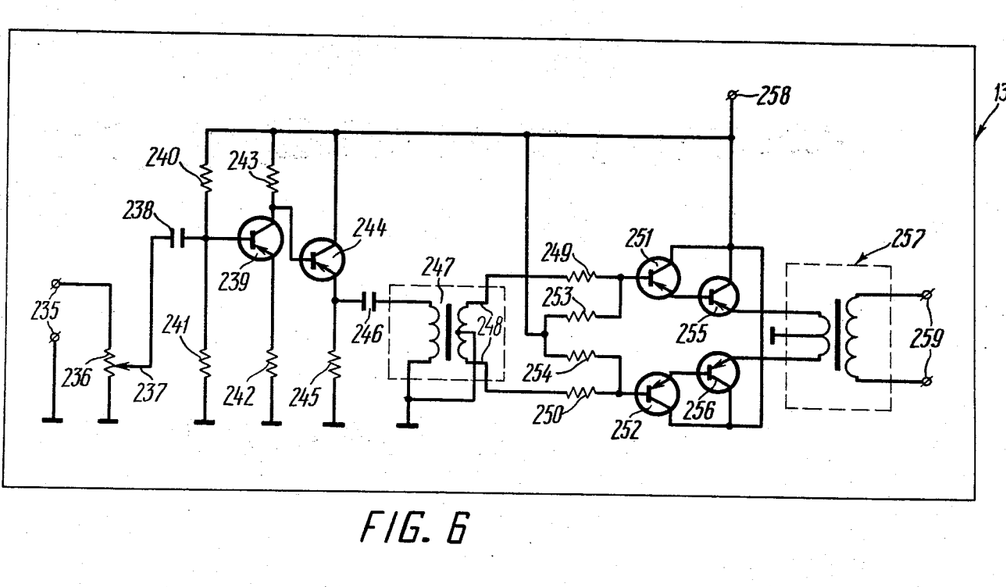
FIG. 6 is a circuit diagram of an A.C. voltage amplifier, according to the invention.

The input 235 (FIG. 6) of the A.C. voltage amplifier 13 (FIG. 1) is connected to a potentiometer 236 (FIG. 6). A slider 237 of the potentiometer 236 is connected through a block capacitor 238 to the base of a transistor 239 and to two resistors 240 and 241 which form a voltage divider and determine the D.C. operating conditions of the transistor 239. The emitter circuit of the transistor 239 contains a resistor 242.

The collector of the transistor 239 is connected to a load resistor 243 and to the base of a transistor 244.

The transistor 244 and an emitter resistor 245 form an emitter follower which is loaded through a capacitor 246 by a transformer 247.

A secondary winding 248 of the transformer 247, the midpoint of which is taken to an ground bus, is connected through resistors 249 and 250 to the bases of transistors 251 and 252, respectively.

The resistor 249 together with a resistor 253 and the resistor 250 together with a resistor 254 form a voltage divider which provides and required operating conditions of output transistors 255 and 256 operating into a transformer 257. The transistors 251 and 255 and the transistors 252 and 256 form composite transistors which operate as a push-pull amplifier.

A terminal 258 of the A.C. voltage amplifier 13 (FIG. 1) is connected to the minus terminal of the power supply (not shown).

An output 259 (FIG. 6) of the transformer 257 is the output of the A.C. voltage amplifier 13 (FIG. 1) to which the servomotor 14 is connected.

The electromechanical infralow frequency generator 11 (FIG. 1) comprises a master oscillator 260 (FIG. 7) connected to a synchronous motor 261, mechanically coupled through a multiple gear reduction 262 to a rotary sine-cosine transformer (resolver) 263. A stator winding 264 of the rotary transformer 263 is shorted, while a stator winding 265 is connected to an amplitude-stabilized oscillator 266. A rotor winding 267 of the rotary transformer 263 is connected to a synchronous detector 268 coupled to the oscillator 266 which has the output 11' connected to the member under investigation. A rotor winding 269 of the rotary transformer 263 is loaded by a matching resistor 270. The electromechanical generator 11 is mechanically coupled with the rotor of the rotary transformer 7 by means of the output shaft 10.

The infralow frequency controlled-member transfer function analyzer operates as follows.

The infralow frequency oscillations of the required amplitude and frequency furnished by the generator 11 (FIG. 1) are applied to the member 1 under investigation, which may be any type of controlled process device.

From the member 1 under investigation, the signal to be analyzed is applied in the form of electric voltage to the matching amplifier 2 with an output filter (not shown).

The object of the matching amplifier 2 with the output filter is to amplify the output voltage to a level at which the infralow frequency controlled-member transfer function analyzer measures the parameters of the input signal with the highest possible accuracy and to remove the noise from the signal being analyzed.

The transfer function of the output filter:

$$W_1(P) = K/1 + T.p \qquad (1)$$

where

K — gain of the matching amplifier 2 with the filter;
T — smoothing (integration) time constant;
p — Carson-Heavyside operator.

The phase shift caused by the filter in the signal being analyzed $$\phi_1 = \arctan T.\omega \qquad (2)$$

where $\omega$-angular frequency of the analyzed signal.

To prevent the phase shift $\phi_1$ affecting the signal measurements this phase shift is made constant for the entire range of infralow frequencies, i.e. $\phi_1$ -const. or $T.\omega$=const.

The variable resistor 34 (FIG. 2) in the feedback circuit of the operational amplifier 28 is used to adjust the gain of the matching amplifier 2 prior to the measurements, i.e. to adjust the scale of the indicating instrument 18 (FIG. 1).

The precision potentiometer 29 (FIG. 2) is used to adjust the scale during the measurements when the amplitude of the signal being analyzed changes within wide limits as a function of frequency.

The decade (factor-of-ten) switch 37 which switches the outputs 35 and 36 of the operational amplifier 28 which are formed by the decade voltage divider consisting of resistors 30, 31, the decade switch 55 which switches the resistor groups in the input circuit of the operational amplifier 58, one group consisting of the resistors 39, 40, 41, 42, 43 and 44 and the other of the resistors 45, 46, 47, 48, 49 and 50, the decade switch 63 which switches the resistor groups in the feedback circuit of the operational amplifier 58, one group consisting of the resistors 80, 81, 82, 83, 84 and 85 and the other of the resistors 86, 87, 88, 89, 90 and 91, the decade switch 78 which switches the outputs 70 and 71 of the operational amplifier 58 which are formed by the decade voltage divider consisting of the resistors 67, 68 and 69, the decade switch 60 which switches the capacitors 75, 76 and 77 in the feedback circuit of the operational amplifier 58 and the decade switch 66 which switches the outputs 64 and 70, of the operational amplifier 58 are used to vary the smoothing (integration) constant of the filter by a factor of ten when the frequency of the infralow frequency generator 11 (FIG. 1) is simultaneously varied by a factor of ten, so as to ensure that K = const. and T.$\omega$ = const.

The intradecade switches 51 and 52 (FIG. 2) which connect one of the resistors 39, 40, 41, 42, 43, 44, 45, 46, 47, 48, 49 and 50 to the input circuit of the operational amplifier 58 and the intradecade switches 92 and 93 which connect one of the resistors 80, 81, 82, 83, 84, 85, 86, 87, 88, 89, 90 and 91 to the feedback circuit of the operational amplifier 58 vary the smoothing (integration) constant of the filter when the frequency of the infralow frequency generator 11 (FIG. 1) simultaneously varied within one decade, so as to insure that K = const. and T.$\omega$ = const.

The switch 73 (FIG. 2) is used to discharge the capacitors 75, 76, 77 through the resistor 61 prior to the measurements.

The transfer function $W_1 (p)$ of the matching amplifier 2 is equal to:

$$W_1(p) = K_1 \cdot \frac{K_2 \cdot K_3}{1+K_3 \cdot R_1 \cdot K_4 \cdot C_1 p} = \frac{K}{1+T \cdot p} \qquad (3)$$

where $$K = K_1.K_2.K_3 \qquad (4)$$

$$T = K_3.R_1.K_4.C_1 \qquad (5)$$

where $K_1$ —gain of the amplifier which includes the operational amplifier 28, the resistors 26, 33, 30, 31, the variable resistor 34 and the precision potentiometer 29;

$$K_2 = R_1/R_2 \qquad (6)$$

$R_1$ — resistance connected in the feedback circuit of the operational amplifier 58;
$R_2$ — resistance connected in the input circuit of the operational amplifier 58;
$K_3$ — ratio of the voltage at the output 64 of the operational amplifier to the voltage at the output 70 (71) of the same amplifier 58 to which the feedback resistor of the operational amplifier 58 is connected;
$K_4$ — ratio of the voltage at the output 64 of the operational amplifier 58 to the voltage at the output 64 (70) of the same amplifier 58 to which to one of the feedback capacitors 75, 76, 77 of the operational amplifier 58 is connected;
$C_1$ — capacitance connected in the feedback circuit of the operational amplifier 58.

The output 65 of the matching amplifier 2 (FIG. 1) is connected to the differentiator 3 and the smoothing filter 4. (FIG. 3): The differentiator 3 carries out differentiation and smoothing of the following voltage applied to the input 96 (FIG.3):

$$U_1.\sin(\omega t-\phi_0-\phi_1) \qquad (7)$$

where
$\phi_0$ — phase angle of the signal being analyzed;
$U_1$ — voltage amplitude;
$t$ — time.

The transfer function of the differentiator 3 (FIG. 1) is equal to:

$$W_2(p) = \frac{T\delta \cdot p}{(1+T_1 p)(1+T_2 p)} \qquad (8)$$

where
$T\gamma$ — differentiation time constant;
$T_1, T_2$ — smoothing time constants.

The following steady voltage appears at the output 157 of the differentiator 3 (FIG. 1) when the transients are over:

$$U_2.\cos(\omega t -\phi_0-\phi_1-\phi_2) \qquad (9)$$

where $U_2$ — voltage amplitude proportional to the amplitude of the signal being analyzed.

$$= \text{arctg } T_1 \cdot \omega + \text{arctg } T_2 \cdot \omega \text{ arctg } T_1 \cdot \omega \qquad (10)$$

as $T_2 \ll T_1$.

The characteristic T.w of the differentiator 3 (FIG. 1) and the phase shift $\phi_2$ remain constant within the entire range of infralow frequencies, i.e.

$$T_\gamma \cdot w = \text{const.}, \; T_1 \cdot \omega = \text{const.}$$

$$T = R_3 \cdot C \cdot K \cdot R_{155}/R_{151} \qquad (11)$$

$$T_1 = R_4 \cdot C \qquad (12)$$

$$T_2 = \frac{R_{156} \cdot R_5}{R_{156} + R_5} C_{158} \qquad (13)$$

where $R_3$ — resistance in the feedback circuit of the operational amplifier 124;

$C_\gamma$ — capacitance in the input circuit of the operational amplifier 124;

$K_\gamma$ — ratio of the voltage at the output 127 of the operational amplifier 124 to the voltage at one of the outputs 139, 140, 141, 142, 143, 144, to which the feedback resistor is connected;

$R_{155}$ — value of resistor 155;

$R_{151}$ — value of resistor 151;

$R_4$ — resistance connected in series with a capacitor to the input circuit of the operational amplifier 124;

$R_{156}$ — value of resistor 156;

$R_5$ — load resistance connected to the output 157;

$C_{158}$ — value of the capacitor 158.

The decade switch 113 (FIG. 3) which switches the resistor groups in the input circuit of the operational amplifier 124, the decade switch 121 which switches the capacitors 118 and 119, 120, the decade switch 126 which switches the resistors 147 and 148, in the feedback circuit of the operational amplifier 124, the decade switch 49 which varies $K_\gamma$ by shorting the resistors 128 and 129 insure that $$T_\gamma \cdot \omega = \text{const.}, T_1 \cdot \omega = \text{const.}$$

when the frequency of the signal being analyzed is varied in decade steps.

The intradecade switches 109 and 110 which switch the resistors 97, 98, 99, 100, 101 and 102 and the resistors 103, 104 and 105, 106, 107 and 108 in the input circuit of the operational amplifier 124 and the intradecade switch 145 which switches the outputs 139, 140, 141, 142, 143 and 144 to which one of the feedback resistors 147 and 148, is connected insure that $T_\gamma \cdot \omega = \text{const.}$ and $T_1 \cdot \omega = \text{const.}$ when the frequency of the signal being analyzed is varied within one decade.

The resistor 156 and the capacitor 158 render operation of the operational amplifier 153 (FIG. 3) unaffected by the switching voltage surges of the modulator 5 (FIG. 1) connected to the output 157 of the differentiator 3 (FIG. 1).

This switch 117 is used to discharge the capacitors 118, 119 and 120, through the resistors 115 prior to the measurements.

The output voltage of the matching amplifier 2 (FIG. 1) is also applied to the input 159 (FIG. 4) of the matching filter 4 with a transfer function $$W_3(p) = K_5/(1+T_3 \cdot p)(1+T_4 \cdot p) \qquad (14)$$

where $$K_5 = R_6/R_7 = T \cdot \omega \qquad (15)$$

$$T_3 = C_2 \cdot R_6 = T_1 \qquad (16)$$

$$T_4 = R_{207} \cdot R_8/R_{207}+R_8 \cdot C_{209} = T_2 \qquad (17)$$

where $R_6$ — resistance in the feedback circuit of operational amplifier 179;

$R_7$ — resistance in the input circuit of the operational amplifier 179;

$C_2$ — capacitance in the feedback circuit of the operational amplifier 179;

$R_{207}$— value of the resistor 207;

$R_8$ — load resistance connected to the input 208;

$C_{209}$ — value of the capacitor 209.

The decade switch 176 which switches the resistor groups in the input circuit, the decade switch 197 which switches the resistor groups in the feedback circuit of the operational amplifier 179 and the switch 201 which switches the capacitors 202, 203 and 204 in the feedback circuit of the operational amplifier 179 insure that $T_3 \cdot \omega = \text{const.} = T_1 \cdot \omega$ when the frequency of the signal being analyzed is varied in decade steps.

The intradecade switches 172 and 173 which respectively switch the resistors 160, 161, 162, 163, 164 and 165 and the resistors 166, 167, 168, 169, 170 and 171 in the input circuit and the intradecade switches 187 and 194 which respectively switch the resistors 181, 182, 183, 184, 185 and 186 and the resistors 188, 189, 190, 191, 192 and 193 in the feedback circuit of the operational amplifier 179 are used to insure that $T_3 \cdot \omega = \text{const.} = T_1 \cdot \omega$ when the frequency of the signal being analyzed is varied within one decade.

The switch 180 is used to discharge the capacitors 202, 203 and 204 through the resistors 206 prior to the measurements. The resistor 207 and the capacitor 209 render operation of the operational amplifier 179 unaffected by the switching voltage surges of the modulator 8 (FIG. 1) connected to the output 208 (FIG. 4).

The resistor 207 and the capacitor 209 perform the same functions as the resistors 156 (FIG. 3) and the capacitors 158.

The steady voltage which appears at the output 208 (FIG. 4) after the transients are over is equal to $$U_2 \cdot \sin(\omega t - \phi_0 - \phi_1 - \phi_2) \qquad (18)$$

The output 208 of the smoothing filter 4 (FIG. 1) is connected to the modulator 8 which is similar to the modulator 5 connected to the differentiator 3.

The reference frequency voltage present at the windings 229 and 232 (FIG. 5) of the transformer 230 of the modulator 5 (FIG. 1) causes the diode bridges alternately to become conductive and non-conductive depending on the instantaneous phase of the reference voltage. At the instant when the diode bridge formed by the diodes 213, 214, 215 and 216, the resistors 217 and 218 and the potentiometer 219 is conductive the diode bridge formed by the diodes 221, 222, 223 and 224, the resistors 225 and 226 and the potentiometer 227 is non-conductive and at the next instant when the diode bridge formed by the diodes 213, 214, 215 and 216, the resistors 217 and 218, and the potentiometer 219 is non-conductive the diode bridge formed by the diodes 221, 222, 223 and 224, the resistors 225 and 226 and the potentiometer 227 is conductive.

The magnitude of the current flowing through the conducting diode bridge is determined by the voltage at the windings 229 and 232 of the transformer 230 and by the values of the resistors 228 and 231, respectively.

The resistors 217 and 218 and the potentiometer 219 are used to obtain a zero voltage across the diagonal of the conducting diode bridge between the junction point of the resistors 217 and 218 and the slider of the potentiometer 219, i.e. at the output 210. The resistors 225 and 226 and the potentiometer 227 are also used to obtain a zero voltage at the output 210 when the current flow through the diodes 221, 222, 223 and 224 and the ballast resistor 231 is caused only by the voltage at the winding 232 of the transformer 230.

The infralow frequency voltage fed to the input 210 is alternately applied through the diode bridges that are rendered conducting, to the windings 211 and 220 of the transformer 212 so that the secondary winding 234 of this transformer develops a reference-frequency voltage, the amplitude of which is proportional to the instantaneous value of the infralow frequency voltage fed to the input 210 from the differentiator 3 (FIG. 1).

The voltage $U_2 \cdot \cos(\omega t - \phi_0 - \phi_1 - \phi_2)$ modulated by the modulator 5 is applied to the rotor winding 6 of the rotary transformer 7.

From the smoothing filter 4 (FIG. 1) the voltage $U_2 \cdot \sin(\omega t - \phi_0 - \phi_1 - \phi_2)$ modulated by the modulator 8 is applied to the rotor winding 9 of the rotary transformer 7.

The voltage at the rotor windings 6 and 9 induces in the stator winding 12 of the rotary transformer 7 a voltage $U_{C-12}$:

$$U_{C-12} = K_1 \cdot [U_2 \cdot \sin(\omega t - \phi_0 - \phi_1 - \phi_2)\cos\alpha - U_2 \cdot \cos(\omega t - \phi_0 - \phi_1 - \phi_2)\sin\alpha] \quad (19)$$

where
$\alpha = \omega t - \phi_1 - \phi_2$ — turn angle of the rotor of the rotary transformer 7 mechanically coupled to the output shaft 10 of the electromechanical infralow frequency generator 11;
$K_T$ — transformation ratio of the rotary transformer 7.

The voltage induced in the stator winding 12 is amplified by the amplifier 13 operating into the servomotor 14 which drives the stator of the rotary transformer 7 through an angle $\phi$ to insure that $U_{C-12} = 0$, i.e.

$$U_{C-12} = K_T \cdot [U_2 \cdot \sin(\omega t - \phi_0 - \phi_1 - \phi_2) \cdot \cos(\omega t - \phi_1 - \phi_2 - \phi\lambda) - U_2 \cdot \cos(\omega t - \phi_0 - \phi_1 - \phi_2) \cdot \sin(\omega t - \phi_1 - \phi_2 - \phi)] = 0 \quad (20)$$

whence $\phi = \phi_0$, i.e. the turn angle of the stator of the rotary transformer 7 is equal to the unknown phase angle $\phi_0$ of the analyzed signal at the output of the member under investigation.

The voltage at the rotor windings 6, 9 induces in the stator winding 16 of the rotary transformer 7 a voltage $U_{C-16}$ $$U_{C-16} = K_T \cdot [U_2 \cdot \cos(\omega t - \phi_0 - \phi_1 - \phi) + U_2 \cdot \sin(\omega t - \phi_0 - \phi_1 - \phi_2)] \quad (21)$$

or, when $\phi = \phi_0$ $$U_{C-16} = K_T \cdot U_2 \cdot [\cos^2(\omega t - \phi_0 - \phi_1 - \phi_2) + \sin^2(\omega t - \phi_0 - \phi_1 \phi_2)] = K_T \cdot U_2 \quad (22)$$

i.e. the voltage induced in the stator winding 16 is proportional to the amplitude of the analyzed signal regardless of the time parameter $t$ (time-invariant voltage).

The voltage induced in the stator winding 16 of the rotary transformer 7 is applied through the switch 17 to the indicating instrument 18 graduated so as to read the amplitude of the signal being analyzed.

The voltage induced in the stator winding 12 of the rotary transformer 7 is applied to the input 235 (FIG. 6) of the A.C. voltage amplifier 13. From the slider 237 of the potentiometer 236 the voltage is applied through the block capacitor 238 to the base of the transistor 239, the operating conditions of which are determined by the voltage divider formed by the resistors 240 and 241 and by the feedback resistor 242. From the load resistor 243 the amplified voltage is applied to the emitter follower using the transistor 245 with the transformer 247 connected in parallel through the block capacitor 246.

The voltage induced in the secondary winding 248 of the transformer 247 is amplified by the push-pull amplifier using the transistors 251, 252, 255 and 256 with the resistors 249, 250, 253 and 254 which determine the D.C. operating conditions of the transistors 251, 252, 255 and 256, the amplifier being loaded into the transformer 257.

The voltage induced in the secondary winding 259 of the transformer 257 is applied to the servomotor 14 (FIG. 1) which drives the stators of the rotary transformers 7 and 15.

The voltage induced in the stator winding 16 of the rotary transformer 7 is applied to the rotor winding 20 of the rotary transformer 15.

Induced in the stator winding 23 of the rotary transformer 15 is a voltage $U_{C-23}$ $$U_{C-23} = K_T \cdot U_2 \cdot K_{T-2} \cdot \cos \phi \quad (23)$$

where
$K_{T-2}$ — transformation ratio of the rotary transformer 15.

The stator of the rotary transformer 15, the rotor of which is locked, is turned by the servomotor 15 through the angle $\phi$ simultaneously with the stator of the rotary transformer 7. When $\phi = \phi_0$ $$U_{C-23} = K_T \cdot K_{T-2} \cdot \cos \phi_0 \quad (24)$$

i.e. the voltage at the stator winding 23 of the rotary transformer 15 is proportional to the real component of the signal being analyzed.

This voltage is applied through the switch 17 to the indicating instrument 18.

When $\phi = \phi_0$ a voltage $U_{C-24}$ is induced in the stator winding 24:

$$U_{C-24} = K_T \cdot K_{T-2} \cdot \sin \phi_0 \quad (25)$$

i.e. the voltage at the stator winding 24 of the rotary transformer 15 is proportional to the imaginary component of the signal being analyzed. This voltage is also applied to the indicating instrument 18 through the switch 17.

The indicating instrument 18 reads the amplitudes of the signal being analyzed as well as its real and imaginary components.

The means 19 calibrated in phase angle units and mounted on the stator of the rotary transformer 7 reads the unknown phase angle of the analyzed signal at the output of the plant 1 under investigation, the plant input being fed with a voltage of a specified amplitude and frequency from the output 11' of the electromechanical infralow frequency generator.

The electromechanical infralow frequency generator 11 comprises the master oscillator 260 (FIG. 7) to which the synchronous motor 261 is connected.

Figure 7:
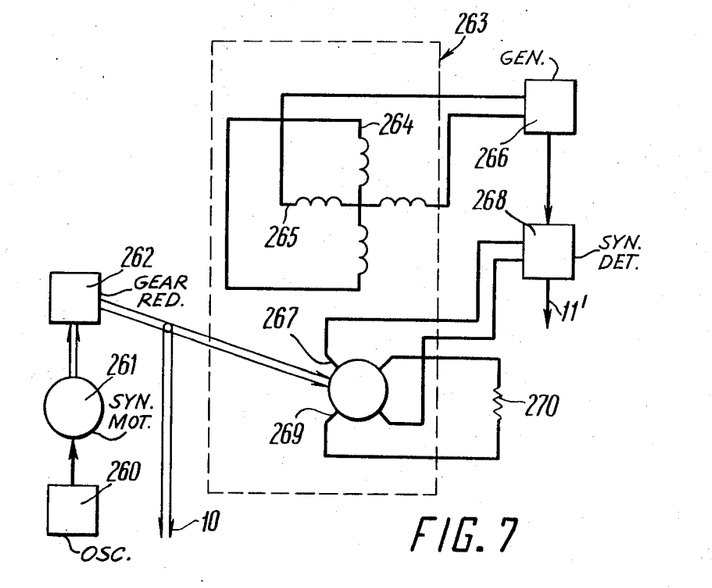
FIG. 7 is a circuit diagram of an infralow frequency electromechanical generator amplifier, according to the invention.

The synchronous motor 261 rotates through the multiple gear reduction 262 the rotor of the rotary sine-cosine transformer (resolver) 263 and through the output shaft 10 the rotor of the rotary transformer 7.

The stator winding 265 of the rotary transformer 263 is fed with an amplitude-stabilized voltage from the generator 266 which also supplies the synchronous detector 268. The sine rotor winding 267 of the rotary transformer 263 is connected to the synchronous detector 268.

From the output of the synchronous detector the voltage of a specified amplitude and frequency is applied to the input of the member 1 under investigation (FIG. 1).

The infralow frequency controlled-member transfer function analyzer has a filter connected at the matching amplifier output, the amplitude-frequency characteristic of the filter being selected so as to take account of the spectral distribution of noise in the signal being analyzed.

The analyzing section of the infralow frequency transfer function analyzer using two rotary transformers measures four basic characteristics of the signal being analyzed regardless of the time and the period of the analyzed signal.

The time required for measuring the signal parameters is mainly determined by the duration of the transients in the filters used in the infralow frequency analyzer.

What is claimed is:

1. An infralow frequency controlled-member transfer function analyzer comprising an electromechanical infralow frequency generator which includes an output shaft; a rotary transformer which includes a rotor including two rotor windings and a stator including two stator windings, said rotor being mechanically coupled to said output shaft of said electromechanical infralow frequency generator; a modulator connected and feeding an output to said rotary transformer; a matching amplifier adapted for being coupled to said controlled member to receive a signal therefrom; a differentiator connected to said matching amplifier and through said modulator to said rotor winding of said rotary transformer; a second modulator; a smoothing filter connected to said matching amplifier in parallel with said differentiator and through said second modulator to said rotor winding of said rotary transformer; a servomotor which drives said stator of said rotary transformer, said stator of said rotary transformer including a means indicating the phase angle of the signal at the output of the controlled member under investigation; an A.C. amplifier connected to said servomotor and to one of said stator windings of said rotary transformer; a switch; an indicating instrument which indicates the amplitude of the signal at the output of the controlled member under investigation, said instrument being connected through said switch to the other of said stator windings of said rotary transformer.

2. An infralow frequency analyzer as claimed in claim 1 which comprises a second rotary transformer including a stator including two stator windings and a rotor with two rotor windings; said stator of said rotary transformer being mechanically coupled to said stator of said first rotary transformer; said stator windings of said second rotary transformer being alternately connected through said switch to said indicating instrument; a matching resistor, one of said rotary windings of said second rotary transformer being shorted through said matching resistor; the other of said rotary windings being connected to said second stator winding of said first rotary transformer.

* * * * *